(12) United States Patent
Louwrier

(10) Patent No.: US 6,479,264 B1
(45) Date of Patent: Nov. 12, 2002

(54) REVERSIBLE INACTIVATION ENZYMES

(75) Inventor: Ariel Louwrier, Surrey (GB)

(73) Assignee: Advanced Biotechnologies Limited, Epsom (GB)

( * ) Notice: Subject to any disclaimer, the term of this patent is extended or adjusted under 35 U.S.C. 154(b) by 0 days.

(21) Appl. No.: 09/649,707

(22) Filed: Aug. 25, 2000

(30) Foreign Application Priority Data

Aug. 27, 1999 (GB) .............................................. 9920194

(51) Int. Cl.[7] .............................. C12N 9/00; C12N 9/99; C12P 19/34; C08H 1/00
(52) U.S. Cl. ....................... 435/183; 435/184; 435/91.2; 530/411
(58) Field of Search ............................. 435/91.2, 183.4; 530/411

(56) References Cited

U.S. PATENT DOCUMENTS 5,262,525 A * 11/1993 Bonnaffe et al. ........... 530/411
5,677,152 A * 10/1997 Birch et al. ................ 435/91.2

* cited by examiner

*Primary Examiner*—Kenneth R. Horlick
*Assistant Examiner*—Teresa Strzelecka
(74) *Attorney, Agent, or Firm*—Galgano & Burke

(57) ABSTRACT

A method for reversibly inactivating thermostable DNA polymerase or ligase, which method comprises reacting a mixture of the thermostable DNA polymerase or ligase with a dicarboxylic acid anhydride, wherein the reaction is carried out using a dried DNA polymerase or ligase in an anhydrous aprotic organic solvent, the dicarboxylic acid anhydride being also substantially anhydrous, whereby the reaction results in essentially complete inactivation of enzyme activity.

5 Claims, 2 Drawing Sheets citraconic anhydride          cis-aconitic anhydride citraconic anhydride dissolved in solvent | lysine residue. solid phase | modified lysine residues, solid phase heat/water lysine residue          citraconic acid

REVERSIBLE INACTIVATION ENZYMES

FIELD OF THE INVENTION

The present invention relates to a method for reversibly inactivating enzymes and, in particular, for reversibly inactivating DNA polymerases and ligases.

BACKGROUND TO THE INVENTION

The DNA polymerase isolated from *Thermus aquaticus* (Taq) is widely used in the polymerase chain reaction (PCR) to amplify small amounts of DNA and RNA (with reverse transcriptase in RT-PCR) by many orders of magnitude. Being a thermostable protein, it is resistant although not totally unaffected by the heat denaturation required to create single-stranded DNA from double-stranded DNA.

The PCR process itself requires four distinct phases. First, an initial DNA denaturation step, generally between 92°–96° C. for 2–4 minutes. This is followed by another, short denaturation step (10 seconds at 92°–96° C.), after which the primers, being short segments of DNA that are chemically synthesised to anneal very specifically to a complementary stretch of single-stranded (denatured) DNA, are allowed to anneal to the denatured DNA. The final stage is the extension step, which occurs at 72° C. for a length of time dependent on the length of the DNA strand that needs to be synthesised. The latter 3 stages are cycled 20–30 times. Hence, each cycle of the latter three stages produces twice as many of the desired DNA fragments, resulting in an exponential increase ($2^n$, where n=the number of cycles) in PCR product.

All four of the described stages rely on accurate temperature control in order to be accomplished properly. A variety of thermocyclers are commercially available to achieve this. Clearly, temperature control is imperative in the denaturation stages, as too low a temperature will not generate a sufficient amount of the required single stranded DNA template, whereas too high a temperature will destroy enzyme activity, which is rapidly inactivated above 94°–95° C. Similarly, if the temperature is too low during the annealing step, the primer will bind non-specifically to the DNA, resulting in the exponential amplification of non-specific products. Too high a temperature will not allow primer-template annealing at all, and hence no product formation. Finally, the extension step at 72° C. is an enzymatic optimum, allowing the maximum amount of product to be synthesised. Clearly, variations from that optimum will reduce PCR product yields.

Although sophisticated computer packages are available to aid in primer design, and a high level of thermal control is available on commercial thermocyclers, the problem of non-specific primer annealing persists. The principal reason for this remains the fact that when the reactants are mixed together the temperature is sub-optimal, encouraging primer-template annealing. During the subsequent elapsed time before the first denaturation temperature is reached, a small amount of non-specific annealing and extension takes place, ultimately resulting in contaminating non-specific product formation.

Currently, a number of laborious, expensive and time-consuming approaches are available to alleviate this problem. These "Hot Start" methods include physically separating reactants until annealing temperatures are reached, either manually or by using wax, see In Innes, M. A., Gelfand, H. D., Sninsky, J. J. and White T. J. (Ed.), PCR Protocols, a Guide to Methods and Applications. Academic Press, California, USA. These not only introduce a lot of extra time into the experimental process but can introduce contaminants, due to the wax barrier itself or the requirement of opening the reaction vessel once some of the reactants have already been mixed and heated.

As discussed in Kellog, D. E. et al. (1994) *Biotechniques* 16,1134–1137, an antibody, specific for the active site of the enzyme is available (binding and inhibiting activity at low temperatures but becoming denatured at high temperatures), but has proved to be expensive as well as being unable to create a graduated activation response, since all the antibody will be denatured at once.

A reversibly inactivated chemically-modified version of the enzyme is available, as described and illustrated in U.S. Pat. No. 5,677,152. The contents of that prior patent are incorporated herein in their entirety by reference.

The chemically modified enzyme of that US patent is synthesised using a single phase water-based system in which both the enzyme and reagent, dicarboxylic acid anhydride, are dissolved. However, the method of preparing the modified enzyme has very strict pH, temperature and reagent excess constraints, principally because the dicarboxylic acid anhydride modifier reagent spontaneously hydrolyses in water (to form an acid) under the circumstances in question. Too much anhydride will result in a huge increase in (exothermic) acid formation, a dramatic pH drop and temperature increase, and subsequent enzyme denaturation. Too little and the vast majority of the anhydride will hydrolyse spontaneously and not remain to modify the protein!

The temperature that the reaction can be carried out at is also necessarily very limited, quoted to be below about 25° C. but usually carried out at no higher than 4° C. for a period as long as 12 hours (or overnight), as any increase in temperature correspondingly increases the rate of modifier reagent hydrolysis in the water, compounding the pH and enzyme denaturation problem even more. Finally, once successfully completed, the enzyme preparation is contaminated with acid. High temperatures are used to re-activate the enzyme, restoring enzyme activity.

It is a general objective of the present invention to provide a method by which a thermostable enzyme, used to amplify nucleic acids with a large reduction in non-specific product formation, can be synthesised in an inactive form so as to be subsequently activated by high temperatures, where the highlighted major problems illustrated above can be avoided.

SUMMARY OF THE INVENTION

According to a first apect of the present invention there is provided a method for reversibly inactivating thermostable DNA polymerase or ligase, which method comprises reacting a mixture of the thermostable DNA polymerase or ligase with a dicarboxylic acid anhydride, wherein the reaction is carried out using a dried DNA polymerase or ligase in an anhydrous aprotic organic solvent, the dicarboxylic acid anhydride being also substantially anhydrous, whereby the reaction results in essentially complete inactivation of enzyme activity.

Preferably the dried DNA polymerase or ligase is first suspended in the aprotic organic solvent and then to this the substantially anhydrous dicarboxylic acid anhydride is added for the reaction to take place. The reaction is suitably carried out at a temperature greater than about 30° C.

Preferably the method comprises the further step of separating the solid phase comprising the revesibly inactivated enzyme from the liquid phase comprising the aprotic organic solvent and washing the solid phase with organic solvent.

Suitably following washing, the reversibly inactivated enzyme is dried.

The anhydrous aprotic organic solvent is preferably selected from the group comprising t-methyl butyl ether (t-MBE), butyl ether, carbon tetrachloride, cyclohexanone, ethyl acetate, methyl ethyl ketone, methyl pentanone, propyl ether, pyridine and sulfolane.

According to a second aspect of the present invention there is provided a reversibly inactivated DNA polymerase or ligase prepared by the method above.

According to a third aspect of the present invention there is provided a kit for carrying out a polymerase chain reaction comprising a reversibly inactivated DNA polymerase as defined above.

BRIEF DESCRIPTION OF THE DRAWINGS

Preferred embodiments of the present invention will now be more particularly described by way of example, and with reference to the accompanying drawings, wherein.

DESCRIPTION OF THE PREFERRED EMBODIMENTS

The system of the present invention involves the chemical modification of a thermostable DNA polymerase by use of a dicarboxylic acid anhydride as modification reagent to render the polymerase reversibly inactive.

The term "thermostable enzyme" refers to an enzyme that is relatively stable to heat and which can withstand the higher temperatures used to remove the modifier groups, typically greater than 50° C., without suffering an irreversible loss of activity. Suitable thermostable DNA polymerases include, for example, those derived from bacteria such as Thermus aquaticus, Thermus thermophilus and Thermotoga maritima.

The chemical modification of the DNA polymerase is carried out on a solid and dried amorphous or crystalline formulation of the enzyme, with about. 5–10% or less water content, suitably in the presence of lyoprotectants. Lyoprotectants are generally substances such as carbohydrates that can aid in protecting the native structure of an enzyme during drying of the enzyme (Dabulis, K. and Klibanov, A. (1993) *Biotechnol. Bioeng.* 41,566–571). The drying can readily be achieved by using (but not limited to) a freeze-drier, vacuum dryer (ambient temperatures used) or a spray-drying system.

The dried enzyme formulation is firstly immersed in an aprotic anhydrous organic solvent which will not react with the modifier reagent, but in which the modification reagent will suitably be fully soluble at the concentration to be used. Examples of solvents include t-methyl butyl ether (t-MBE), butyl ether, carbon tetrachloride, cyclohexanone, ethyl acetate, methyl ethyl ketone, methyl pentanone, propyl ether, pyridine and sulfolane.

Figure 2:
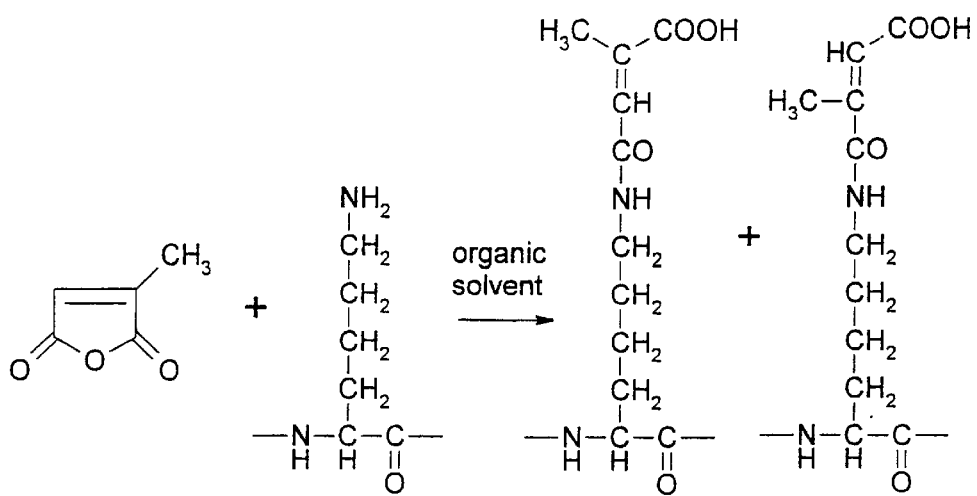
FIG. 2 shows the reaction of citraconic acid anhydride with lysine residues (of a DNA strand) in an organic solvent.

The dicarboxylic acid anhydride that comprises the modification reagent and that is then added is preferably soluble in the solvent for reaction efficiency (surfactant may also be used) but the solvent selected preferably cannot appreciably solubilize the enzyme, so that a two-phase system of solid enzyme suspension in an anhydrous organic solvent (plus dissolved modifier reagent) exists, greatly facilitating separation of the modified enzyme at the end of the reaction See Example 1 hereinafter for a detailed description of an example of the overall procedure. After the reaction (FIG. 2) is completed (which takes only a few hours), the enzyme formulation is washed several times in a compatible organic solvent (e.g. hexane) or solvent mixture to remove any residual dicarboxylic acid anhydride modification reagent, after which it is dried (e.g. under vacuum, or at 30–70° C.).

Figure 3:
FIG. 3 shows the reaction of the modified lysine residues with water when heated.
Figure 3:
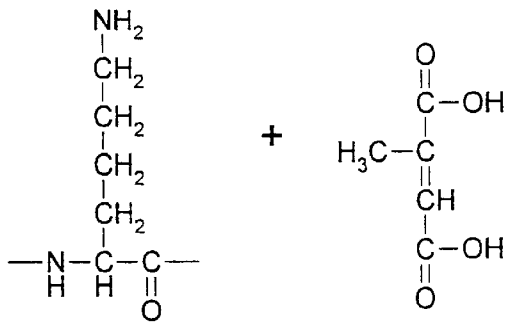

The drying removes any residual modifier reagent that might contaminate the preparation. Once these steps are complete, the known quantity of modified enzyme can be re-dissolved in aqueous solution, or stored as the dried powder. When heated in aqueous solution (during use), the inactivated enzyme will revert to its native, active form (FIG. 3).

Figure 1:
FIG. 1 shows the structures of citraconic acid anhydride and cis-aconitic anhydride.

The modification reagent, dicarboxylic acid anhydride, may, for example, be citraconic anhydride or cis-aconitic anhydride (FIG. 1) both of which can dissolve in the anhydrous aprotic organic solvent.

The dicarboxylic acid anyhydride used is suitably one having the general formula:

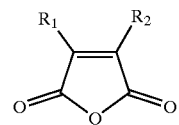

where $R_1$ and $R_2$ are hydrogen or organic radicals, which may be linked, or of the general formula:

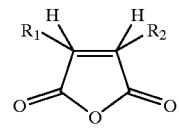

where $R_1$ and $R_2$ are organic radicals, which are preferably linked, and the hydrogen are cis and wherein said reaction results in essentially complete inactivation of enzyme activity.

It might, for example, be maleic anhydride or a tetrahydrophthalic anhydride. However, other dicarboxylic acid anhydrides may also be used as will be apparent to the man skilled in the art. For example, noncyclic dicarboxylic acid anhydrides may be used as the modification reagent.

The use of dried polymerase or ligase together with substantially anhydrous modification reagent and an aprotic anhydrous organic solvent avoids the presence of stray hydrogen ions in solution and so ensures that there can be no pH-based (acid or alkali) denaturation of the enzyme formulation while the enzyme is suspended in the solvent.

The outstanding advantages of this system lie in that the system is substantially entirely free of water, so that the modification reaction (of the lysine groups present on the enzyme) can be directly and easily controlled. There is no pH condition in this non-aqueous system and the reaction can be carried out comparatively very rapidly (five hours and under) at elevated temperatures of about 50° C.

In order to ensure a rapid reaction, large excesses of modification reagent can in this case be easily added without fear of enzyme destruction, as water is essentially absent and will not be present to spontaneously hydrolyse the modifier reagent to the destructive acid by-product.

EXAMPLE 1

The DNA polymerase from *Thermus aquaticus* (50,000 units) is vacuum-dried in the presence of 2% sucrose (lyoprotectant) in double-distilled and de-ionised water. The resulting amorphous powder is then added to 5 mL anhydrous t-MBE, to which an excess of citraconic anhydride is added to modify the lysine groups in question (5% (v/v)). The solvent is then maintained at 37° C. for 5 hours. At this stage the powder is washed 4 times with 10 mL hexane to remove any remaining contaminating modification reagent. Finally, the powder is stored as is at −20° C., 4° C. or dissolved in aqueous solution, or a storage buffer (20 mM Tris-HCl; 100 mM potassium chloride; 0.1 mM ethylenediaminetetraacetic acid; 1 mM dithiothreitol; 0.5% (v/v) Tween 20; 0.5% (v/v) Nonidet P40; 50% glycerol; pH 9.2) to the desired concentration (usually 5 units/µL) and stored at −20° C.

EXAMPLE 2

The DNA polymerase from *Thermus aquaticus* (50,000 units) is freeze-dried in the absence of lyoprotectants in a lightly buffered solution (10 mM Tris-HCl, pH 9.2). The resulting powder is then added to 5 mL anhydrous t-MBE, to which sufficient citraconic anhydride is added to modify the lysine groups in question (5%). The solvent is then maintained at 50° C. for 5 hours. After the reaction is complete, and the powder is washed 4 times with 10 mL hexane to remove any remaining modification reagent. Finally, the powder is stored as is at −20° C., 4° C. or dissolved in aqueous solution, or a storage buffer (20 mM Tris-HCl; 100 mM potassium chloride; 0.1 mM ethylenediaminetetraacetic acid; 1 mM dithiothreitol; 0.5% (v/v) Tween 20; 0.5% (v/v) Nonidet P40; 50% glycerol; pH 9.2) to the desired concentration (usually 5 units/µL) and stored at −20° C.

EXAMPLE 3

The DNA polymerase from *Thermus aquaticus* (50,000 units) is dried or freeze-dried in the presence of 1 M Tris HCl at pH 9.2. The resulting amorphous powder is then added to 5 mL anhydrous ethyl acetate, to which an excess of citraconic anhydride is added to modify the lysine groups in question (5% (v/v)). The solvent is then maintained at 50° C. for 5 hours. At this stage the powder is washed 4 times with 10 mL hexane to remove any remaining contaminating modification reagent. Finally, the powder is stored as is at −20° C., 4° C. or dissolved in aqueous solution, or a storage buffer (20 mM Tris-HCl; 100 mM potassium chloride; 0.1 mM ethylenediaminetetraacetic acid; 1 mM dithiothreitol; 0.5% (v/v) Tween 20; 0.5% (v/v) Nonidet P40; 50% glycerol; pH 9.2) to the desired concentration (usually 5 units/µL) and stored at −20° C.

EXAMPLE 4

The DNA polymerase from *Thermus aquaticus* (50,000 units) is dried or freeze-dried in the presence of 10 mM Tris HCl at pH 9.2. The resulting amorphous powder is then added to 5 mL anhydrous methyl ethyl ketone, to which an excess of citraconic anhydride is added to modify the lysine groups in question (1% (v/v)). The solvent is then maintained at 50° C. for 5 hours. At this stage the powder is washed 4 times with 10 ml hexane to remove any remaining contaminating modification reagent. Finally, the powder is stored as is at −20° C., 4° C. or dissolved in aqueous solution, or a storage buffer (20 mM Tris-HCl; 100 mM potassium chloride; 0.1 mM ethylenediaminetetraacetic acid; 1 mM dithiothreitol; 0.5% (v/v) Tween 20; 0.5% (v/v) Nonidet P40; 50% glycerol; pH 9.2) to the desired concentration (usually 5 units/µL) and stored at −20° C.

EXAMPLE 5

The DNA polymerase from *Thermus aquaticus* (50,000 units) is dried or freeze-dried in the presence of 10 mM Tris HCl at pH 9.2. The resulting amorphous powder is then added to 5 mL anhydrous carbon tetrachloride, to which an excess of citraconic anhydride is added to modify the lysine groups in question (1% (v/v)). The solvent is then maintained at 37° C. for 5 hours. At this stage the powder is washed 4 times with 10 ml hexane to remove any remaining contaminating modification reagent. Finally, the powder is stored as is at −20° C., 4° C. or dissolved in aqueous solution, or a storage buffer (20 mM Tris-HCl; 100 mM potassium chloride; 0.1 mM ethylenediaminetetraacetic acid; 1 mM dithiothreitol; 0.5% (v/v) Tween 20; 0.5% (v/v) Nonidet P40; 50% glycerol; pH 9.2) to the desired concentration (usually 5 units/µL) and stored at −20° C.

RESULTS FOR USE OF THE ENZYMES OF EXAMPLES 1–5

Figure 4:
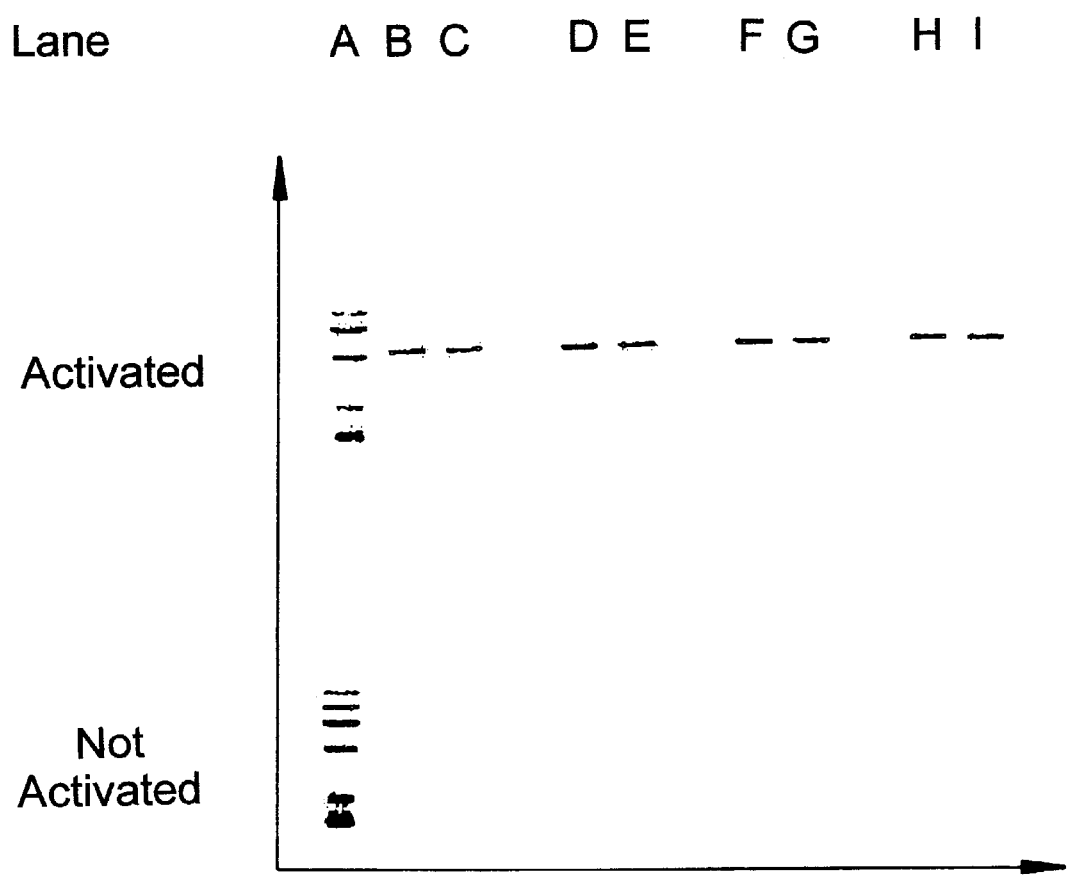
FIG. 4 is a photograph of an agarose gel demonstrating the results of experimental examples that will be described hereinafter.

Once the enzyme powders have been re-dissolved in the appropriate buffers they can be strictly controlled as to the reversibility of the enzyme transformation. Should the DNA polymerases from Examples 1–5 be successfully modified, re-dissolved in aqueous solution at an appropriate concentration, then they will be reactivated by an initial heating step at 95° C. for 15 minutes, after which a PCR can be carried out. If this step is omitted, and the enzyme is modified, then there will be no reaction product. FIG. 4 shows the results of β-actin PCR carried out with and without the activation step, illustrating that all example methods achieve the specified outcome. In FIG. 4 Lane A is for marker whereas, lanes B-C, D-E, F-G, H-I and J-K show PCR results from the examples 1, 2, 3, 4 and 5 respectively, under activated and non-activated conditions.

The experimental PCR conditions for providing the results in FIG. 4 were as follows: All samples were dissolved in buffered aqueous solution (20 mM Tris (pH 8.0); 100 mM KCl; 0.1 mM EDTA; 1 mM DTT; 0.5% Tween 20; 0.5% Nonidet P40; 50% glycerol), before use diluted to 5U/µl before use. Reaction buffer: 10 mM Tris pH 8.3, 50 mM KCl. Activation step (if used) at 95° C. for 15 minutes. The PCR consists of initial denaturation at 94° C. for 2 minutes (1 cycle); denaturation at 94° C. for 20 seconds, annealing at 60° C. for 30 seconds, and extension at 72° C. for 30 seconds (30 cycles); final extension at 72° C. for 5 minutes. Human DNA template concentration was (100 ng/µl); dNTPs (0.2 mM each), 1.5 mM $MgCl_2$; Primer 1 (5'-ATT TGC GGT GGA CGA TGG AG-3') and Primer 2 (5'-AGA GAT GGC CAC GGC TGC TT-3') at 250ng each per reaction.

What is claimed is:

1. A method for reversibly inactivating thermostable DNA polymerase or ligase, which method comprises reacting a mixture of the thermostable DNA polymerase or ligase with a dicarboxylic acid anhydride, wherein the reaction is carried out using a dried DNA polymerase or ligase in an anhydrous aprotic organic solvent, the dicarboxylic acid anhydride being also substantially anhydrous, whereby the reaction results in essentially complete inactivation of enzyme activity, wherein the anhydrous aprotic organic solvent is selected from the group consisting of t-methyl butyl ether (t-MBE), butyl ether, carbon tetrachloride, cyclohexanone, ethyl acetate, methyl ethyl ketone, methyl pentanone, propyl ether, pyridine and sulfolane.

2. The method as claimed in claim 1, wherein the dried DNA polymerase or ligase is first suspended in the aprotic organic solvent and then to this the substantially anhydrous dicarboxylic acid anhydride is added for the reaction to take place.

3. The method of claim 1, wherein the reaction is carried out at a temperature greater than about 30° C.

4. The method as claimed in claim 1 wherein the method comprises the further step of separating comprising the reversibly inactivated enzyme from the aprotic organic solvent and washing the enzyme with organic solvent.

5. The method of claim 1 wherein the reversibly inactivated enzyme is washed and is then dried.

* * * * *